United States Patent [19]
Fabregat

[11] Patent Number: 4,991,616
[45] Date of Patent: Feb. 12, 1991

[54] INSTALLATION FOR THE SUPPLY OF OXYGEN IN HOSPITALS AND THE LIKE

[75] Inventor: Francisco B. Fabregat, Madrid, Spain

[73] Assignee: Desarrollos, Estudios Y Patentes, S.A., Madrid, Spain

[21] Appl. No.: 295,806

[22] Filed: Jan. 11, 1989

[30] Foreign Application Priority Data

Nov. 1, 1988 [ES] Spain ................................ 8800056

[51] Int. Cl.$^5$ ............................................ G05D 11/13
[52] U.S. Cl. ................................ 137/93; 128/203.25; 128/205.11
[58] Field of Search .................... 137/93, 113, 114; 128/203.25, 204.22, 204.29, 205.11, 205.12

[56] References Cited

U.S. PATENT DOCUMENTS

| | | | |
|---|---|---|---|
| 2,547,823 | 4/1951 | Josephian | 137/114 X |
| 3,526,239 | 9/1970 | Oroza | 137/114 X |
| 3,896,837 | 7/1975 | Rohling | 137/113 X |
| 4,072,148 | 2/1978 | Munson et al. | 128/205.11 |
| 4,364,493 | 12/1982 | Raynes et al. | 137/114 X |
| 4,428,372 | 1/1984 | Beysel et al. | 128/205.12 X |
| 4,627,860 | 12/1986 | Rowland | 128/204.22 X |
| 4,651,728 | 3/1987 | Gupta et al. | 128/204.29 X |

*Primary Examiner*—Stephen M. Hepperle
*Attorney, Agent, or Firm*—Davis Hoxie Faithfull & Hapgood

[57] ABSTRACT

The invention relates to an installation for the supply of oxygen in hospitals and the like, formed by a conventional oxygen station and an oxygen generating unit by filtering, a mixing frame, a middle mixture deposit and an emergency frame which allows the substitution of the connection to the middle mixture deposit through connection to an emergency set being established as from these means. The mixing frame in turn incorporates two oxygen analyzers, two pressure controllers, two sensors for the concentration of oxygen, two electrovalves, two control valves activated by a single controller, two channel transducers, two single way valves, two pressure sensors and a small mixture valve.

8 Claims, 2 Drawing Sheets

INSTALLATION FOR THE SUPPLY OF OXYGEN IN HOSPITALS AND THE LIKE

FIELD OF THE INVENTION

The present invention relates to an installation for the supply of oxygen in hospitals and the like which, ensure a full operative reliability, i.e., total lack of risk of interruption of the supply, and allows a substantial economic savings.

BACKGROUND OF THE INVENTION

As is known, oxygen is the most abundant element in nature. It forms part, in a proportion of approximately 21%, of the atmosphere it is found forming part of most minerals and rocks and, of course, is a constituent of all living beings.

In the specific case of animals, oxygen is essential for ensuring organic metabolism, which, in superior vertebrates, and therefore man, takes place through breathing, which consists in the inhalation of atmospheric oxygen through the lungs and the subsequent transport through the bloodstream. As it is a basic life-supporting element it is not surprising that, when considered as a product, oxygen is also essential in manifold medicinal applications. It is therefore essential in many medical processes which require this element as an agent to speed up metabolism. Oxygen therapy and air therapy are well known examples. Oxygen is also used in anesthesia, as well as in open heart surgery, where the patients blood must be directly oxygenated.

In short, it may be said that oxygen is nowadays an essential medical product which may not be lacking in any hospital and which is consumed in far from negligible amounts.

In order to ensure this supply and to enable its distribution throughout the hospital complex, there is a supply station which distributes the product throughout the hospital through an internal distribution network. The supply station is usually composed of by steel cylinders (bottles) which contain the gas under pressure or, more recently, by cryogenic tanks which store liquid oxygen at low temperature and, after vaporization in a heat exchanger, the oxygen is supplied to the hospital network. All the stations have corresponding emergency systems, constituted by a set of bottles which act as a reserve and enter into operation in case of need should the main source suffer a serious breakdown or should there be no supply.

Medicinal oxygen supplied in this way is an expensive product. Its price is determined by two essential factors.

In the first place, it is necessary for its purity to be high, approximately 99.9%, since it is generated in chemical plants with a basic production destined for industrial uses. It is also essential to ensure that the quality of the product sent for hospital consumption is not in any way polluted.

Secondly, consumption of the product by an average hospital, is considerably smaller than in industrial consumption, although the installations required for its storage, and specifically in the case of cryogenic tanks, have similar and considerably high costs, wherefore they have a more significant effect in the price of medicinal oxygen.

It is also necessary to point out that the medicinal application of pure oxygen is practically non-existent. In fact, pure oxygen is a highly toxic product and the continued inhalation thereof causes death. It therefore is normally supplied with air or other gases in variable concentrations of oxygen which very rarely exceed 80%. Most frequently, the oxygen product is provided in a proportion of around 40%. For this reason, American Pharmacopoeia has just authorized the classification of medicinal oxygen as oxygen which does not have an impurity of inert gases of over 7%, and therefore a concentration of oxygen equal to or over 93%.

On the other hand, as previously mentioned, oxygen is a very abundant element, for it is present as such in the atmosphere in a very high proportion, the other components of air being nitrogen and a very small part of argon, apart from traces of other gases.

The possibility of "filtering" air, separating its constituents, was achieved some years ago by means of zeolite filters or membranes, which absorb a gas (generally nitrogen) and allow the rest to pass through. Thus oxygen may be produced, in situ, with a considerably low cost, for only a system of compressors and filters are necessary to produce it, with a reduced maintenance and a likewise low consumption of energy.

The main disadvantage of these units consists in the fact that they cannot produce oxygen with a purity of over 95%, has been eliminated with the mentioned recent authorization of American Pharmacopoeia. The required 93% purity is easily obtained with the main remaining impurity being the inert gas argon.

There is however a further disadvantage in connection with reliability.

It is wholly unthinkable that a hospital may be deprived of the oxygen supply. This condition must be avoided at all costs and any supply system must absolutely prevent this. Autonomous generating units are not satisfactory because they are machines, and as such, are subject to possible breakdowns and stoppings.

It is true that, by duplicating some parts of the system, it is possible to decrease the risk of stopping, but, apart from the fact that total elimination of the risk thereof is impossible, successive accumulation of duplicate or safety elements make the costs of these units so high that the oxygen produced no longer has economic advantages.

DESCRIPTION OF THE INVENTION

The installation of the invention has been designed to eliminate the previously described disadvantages and is based on the combined and complementary use of the two basic solutions for supplying oxygen.

More specifically, said installation comprises an oxygen source or station of the conventional type, either based on bottles or by means of a cryogenic container, and of an oxygen generating unit through the likewise conventional method of filtering.

From these two basic means for obtaining oxygen, a mixing frame is established, behind it a middle mixture deposit and finally an emergency frame which allows the normal connection to the supply network of the middle mixture deposit to be substituted by the connection to an emergency set.

Specifically, the mixing frame is provided with two oxygen analyzers, with a register and a controlling function, two pressure controllers which ensure that the respective outlet pressures are identical, two sensors for detecting the concentration of oxygen, two electrovalves, two control valves activated by a single controller, two flow transducers which send information to the controller for the control valves, two single way valves, two pressure sensors and a small mixture chamber, the functionality whereof will be described later on.

In accordance with this construction, and as shall also be seen subsequently, a full reliability of the installation is obtained in connection with the total lack of risk of a cut in the oxygen supply, and with a reduction of costs which may even reach 50%, with a slight reduction in the oxygen concentration, only 7%.

PREFERRED EMBODIMENT OF THE INVENTION

Figure 1:
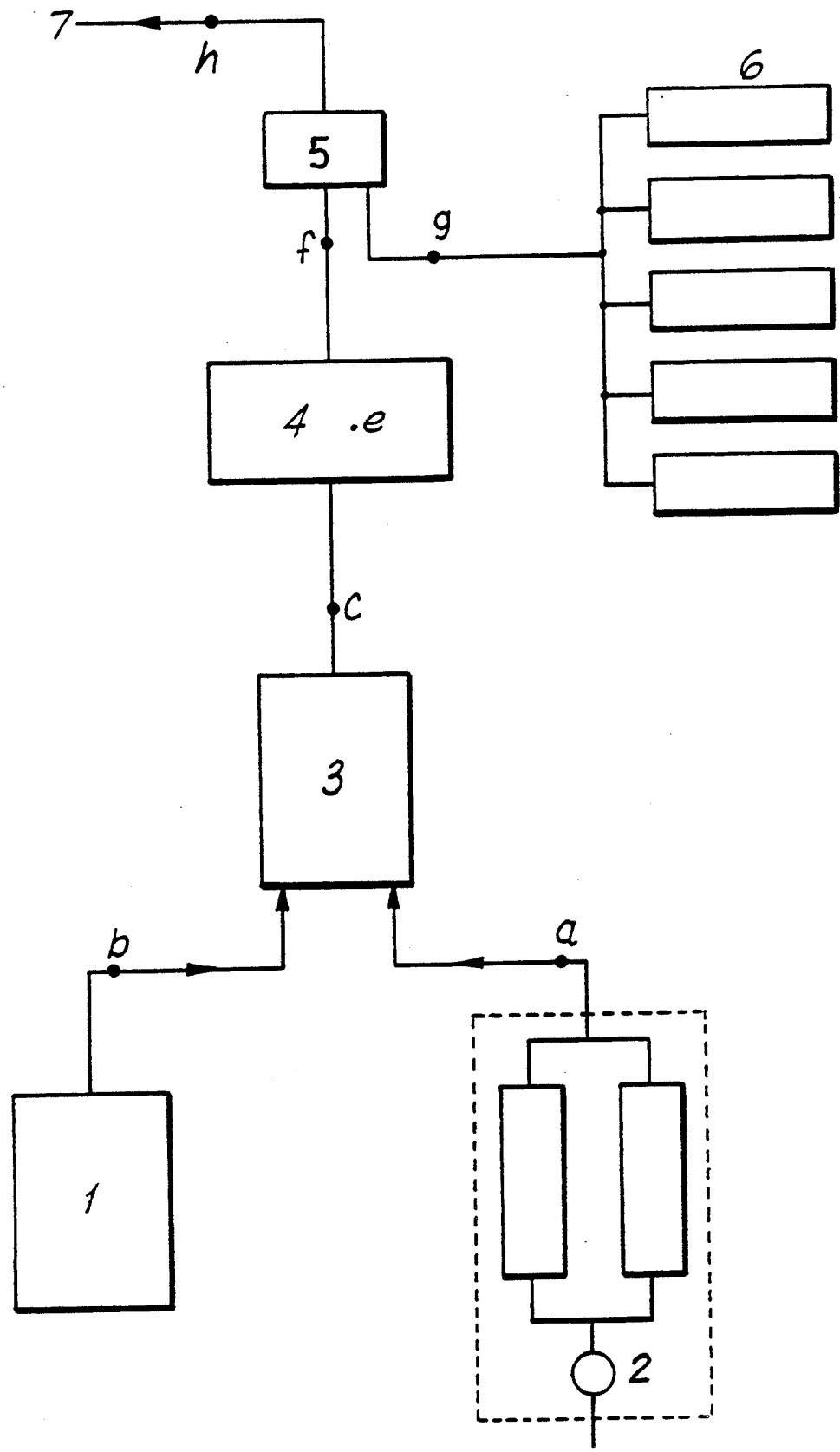
FIG. 1 is a diagrammatic representation, in accordance with a block diagram, of an installation for the supply of oxygen in hospitals and the like, in accordance with the object of the present invention.

In FIG. 1, it may be seen that the installation is comprised by an oxygen source or station 1, being of a conventional type, either of bottles or else materialized in a cryogenic container, and a unit 2 for the generation of oxygen through the likewise conventional method of filtering.

The oxygen station 1 and generating unit 2 are connected to a mixing frame 3, from which the oxygen is led to a middle mixture deposit 4, behind which is placed an emergency frame 5 which allows automatic connection of an emergency set 6 to the installation 7, in the event of a scarcely probable, but possible, emergency.

More specifically, oxygen source 1 supplies oxygen to mixing frame 3 with a flow $Q_1$ and a concentration $Cn_1$, which is practically 100%, whereas generating unit 2 supplies a flow $Q_2$ with a concentration $Cn_2$ to the same frame 3.

Both streams of gas are mixed in frame 3 and a flow $Q_3$ is obtained which is the result of adding $Q_1$ and $Q_2$ and a gas with a concentration $Cn_3$:

$$Cn_3 = \frac{Cn_1 Q_1 + Cn_2 Q_2}{Q_1 + Q_2}$$

The mixture is introduced in the middle deposit 4, which has a considerable capacity, and which acts as a homogenizer and pressure equalizer, from which said mixture goes, through emergency frame 5, to distribution network 7.

The function of emergency frame 5 is, as may be deduced from the foregoing, to detect a possible drop of pressure in the container to below a pre-established minimum limit, which would give rise to the interruption of the flow $Q_3$. After detection, oxygen from emergency set 6 is supplied to the emergency frame 5.

Figure 2:
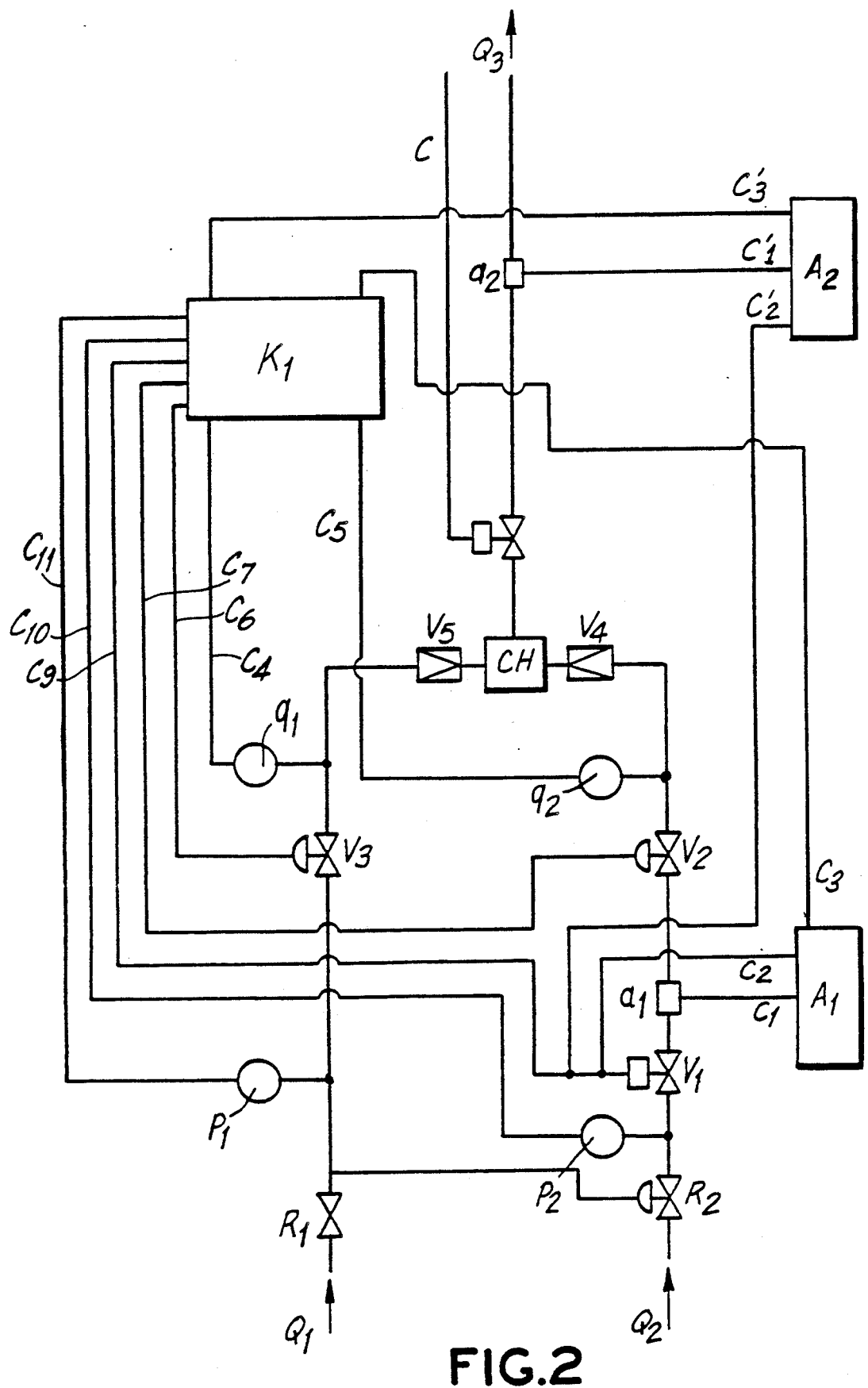
FIG. 2 is a diagrammatic representation of the structure inherent to the mixing frame which takes part in the installation of the previous figure.

From this basic structure for the installation, attention should be called especially to mixing frame 3, which is shown in detail in FIG. 2. The frame is provided with the previously mentioned analyzers, controllers, sensors and transducers and the operation whereof is as follows:

As shown in FIG. 2, the gas from the oxygen station flows through pressure controller $R_1$, the control valve $V_3$, the single way valve $V_5$, and then into the small mixing chamber CH. The gas from the oxygen generating station, similarly, flows through pressure controller $R_2$, the control valve $V_2$, the single way valve $V_4$ and finally into the small mixing chamber CH.

In oxygen analyzers $A_1$ and $A_2$ the minimum values of oxygen concentration considered to be acceptable are introduced. The controller $K_1$ determines the proportion between flows which must exist between line 1 and 2 (i.e., between $Q_1$ and $Q_2$). It should be borne in mind that the point of instructions in $A_2$ is not independent, but is determined by the formula:

$$Cn_3 = \frac{Cn_1 Q_1 + Cn_2 Q_2}{Q_1 + Q_2}$$

and if $Q_1/Q_2 = X$ $$Cn_3 = \frac{Cn_1 X + Cn_2}{1 + X}$$

and if we consider that very approximately $Cn_1 = 100$, $$Cn_3 = \frac{100X + Cn_2}{1 + X}$$

$K_1$, measuring flows through flow transducers $Q_1$ and $Q_2$, will regulate the apertures of control valves of $V_2$ and $V_3$ in order to obtain the mixing relation X, with a minimum predetermined flow of, for example, $Q_1$.

The oxygen station/oxygen generator gas mixture, after being made in the small chamber CH and sensed by oxygen concentration sensor $a_2$ in $a_2$, is led to container 4 and, from here, to the distribution network.

Should, due to some anomaly, pressure sensors $p_1$ and $p_2$ detect different pressures which might affect the mixture, $K_1$ would close electrovalve $V_1$, and the network would be fed only from 1.

Should $A_1$ detect a concentration below that expected through control line $C_1$ from oxygen concentration sensor $a_1$, $A_1$ would close $V_1$ through control line $C_2$. Upon closing $V_1$, $A_1$ would also inform $K_1$ through control line $C_3$, that 100% of the flow should come from the oxygen station.

Similarly, should $A_2$ detect a concentration below that expected from oxygen concentration sensor line $C_2'$. Upon closing $V_1$, $A_1$ would also inform $K_1$ through control line $C_3'$ that 100% of the flow should come from the oxygen station.

There are two analyzers for safety. It is possible to construct cheap oxygen analyzers based on simple chemical sensors but they have the disadvantage of a reduced stability and duration. The existence of two banked units requires a condition of simultaneous triple failure (which is practically impossible: oxygen generator and the two analyzers) for the irregular operation of the unit, wherefore the reliability of the quality of the oxygen supplied is guaranteed.

Finally, in the event of actuation of frame 5, the latter activates electrovalve $V_6$ simultaneously to the introduction of the set of bottles, the system being cut off from the network. failure of the system of the present invention, the only effect will be a greater consumption from the traditional source. This allows us to install a simple and cheap generating source.

The expediency of maintaining the two units in operation is given by the fact that the efficiency of the generators decreases significantly when oxygen is desired with a maximum concentration (95%), for which reason it is convenient not to suppress values of 90% in order to obtain a maximum efficiency.

Under these conditions, the cost of the oxygen including energy consumption, which a generating unit may produce is of around ¼ of the cost of the traditional medicinal oxygen.

The following table may be established, wherein $Cn_2$ represents the oxygen concentration of the gas from the oxygen generator, $Cn_1$ represents the oxygen concentration of the gas from the oxygen source, $Cn_3$ represents the final concentration of the oxygen, $P_3$ represents the price of the final product and $P_1$ represents the price of oxygen supplied by an external supplier. In the table below, $Cn_1$ equals 100% and $Cn_2$ equals 90%. $P_3$, the price of the final product, is determined by the equation below:

$$P_3 = \frac{P_1 (X + 0.25)}{(1 + X)}$$

|  | $X = Q_1/Q_2$ | $Cn_3$ | $P_3$ |
| --- | --- | --- | --- |
| 4 | (80/20) | 98% | 0.85 $P_1$ |
| 1.5 | (60/40) | 96% | 0.7 $P_1$ |
| 1.0 | (50/50) | 95% | 0.625 $P_1$ |
| 0.67 | (40/60) | 94% | 0.55 $P_1$ |
| 0.43 | (30/70) | 93% | 0.47 $P_1$ |

This installation is highly reliable, virtually eliminating the risk of a cut in oxygen supply. The reduction in the costs of the system can reach 50%, while the oxygen concentration is only reduced 7%.

The unit has been described as being apt for hospital use, but it is obvious that it could be used in any other case wherein oxygen with a guaranteed quality, continuous supply and low price were required.

I claim:

1. An installation for the supply of oxygen comprising:
   an oxygen source; an oxygen generating unit;
   a mixing frame for mixing oxygen simultaneously supplied by said oxygen source and said oxygen generating unit;
   an emergency frame for receiving said mixture of oxygen and detecting a drop in pressure below a pre-established limit; and
   an emergency oxygen supply connected to said emergency frame, said emergency oxygen supply being activated to supply oxygen to said emergency frame if said emergency frame detects a drop in pressure, said emergency frame supplying said mixture of oxygen to a distribution network;
   wherein the mixing frame comprises two oxygen analyzers, one for determining the concentration of oxygen in the mixing frame, and the other for determining the concentration of oxygen from the oxygen generating unit, and a controller for controlling the proportion between the oxygen flow from the oxygen source and the oxygen flow from the oxygen generating unit.

2. The installation of claim 1, wherein said oxygen source are bottles.

3. The installation of claim 1, wherein said oxygen source are cryogenic tanks.

4. The installation of claims 1 or 2, wherein the oxygen generating unit provides oxygen through the filtering of air.

5. The installation of claim 1, wherein the concentration of oxygen supplied by the oxygen supply station and the oxygen generating station are different.

6. The installation of claim 1, wherein the minimum acceptable value of oxygen concentration in the mixing frame is stored in one analyzer and the minimum acceptable value of oxygen concentration from the oxygen generating unit is stored in the other analyzer.

7. An installation for the supply of oxygen comprising:
   an oxygen source supplying oxygen stored in bottles;
   an oxygen generating unit providing oxygen through the filtering of air;
   a mixing frame for mixing oxygen simultaneously supplied by said oxygen source and said oxygen generating unit, said mixing frame comprising two oxygen analyzers, one for determining the concentration of oxygen in the mixing frame, and the other for determining the concentration of oxygen from the oxygen generating unit, wherein the minimum acceptable value of oxygen concentration in the mixing frame is stored in one analyzer and the minimum acceptable value of oxygen concentration from the oxygen generating unit is stored in the other oxygen analyzer;
   said mixing frame further comprising a controller for controlling the proportion between the oxygen flow from the oxygen source and the oxygen flow from the oxygen generating unit, said controller controlling two valves, one regulating the flow of oxygen from the oxygen source, the other regulating the flow of oxygen from the oxygen generating unit; two pressure sensors, one for measuring the pressure of the flow oxygen from the oxygen source and the other for measuring the flow of oxygen from the oxygen generating unit; and two pressure controllers for ensuring that the outlet pressures from the oxygen source and oxygen generating units are the same;
   a middle mixture deposit station for receiving said mixture of oxygen from said mixing frame;
   an emergency frame for receiving said mixture of oxygen from said middle mixture deposit station and detecting a drop in pressure below a pre-established limit; and
   an emergency oxygen supply connected to said emergency frame, said emergency oxygen supply being activated to supply oxygen to said emergency frame if said emergency frame detects a drop in pressure, said emergency frame supplying said mixture of oxygen to a distribution network.

8. The installation of claims 1 or 7, wherein the concentration of oxygen supplied by the oxygen source is about 100% and the concentration of oxygen supplied by the oxygen generating unit is about 90%.

* * * * *

UNITED STATES PATENT AND TRADEMARK OFFICE
CERTIFICATE OF CORRECTION

PATENT NO. : 4,991,616
DATED : February 12, 1991
INVENTOR(S) : Fabregat

It is certified that error appears in the above-identified patent and that said Letters Patent is hereby corrected as shown below:

Column 4, line 25, replace "$Q_1$" with --$q_1$--;

Column 4, line 26, replace "$Q_2$" with --$q_2$--;

Column 4, replace the paragraph at lines 44-48 with:

-- Similarly, should $A_2$ detect a concentration below that expected from oxygen concentration sensor $a_2$ through control line $C_1'$, $A_2$ would close $V_1$ through control line $C_2'$. Upon closing $V_1$, $A_1$ would also inform $K_1$ through control line $C_3'$ that 100% of the flow should come from the oxygen station. --; and in Figure 2 of the drawings, add "$V_6$" next to the valve above box "CH".

Signed and Sealed this

Second Day of March, 1993

Attest:

STEPHEN G. KUNIN

*Attesting Officer*  *Acting Commissioner of Patents and Trademarks*